(12) United States Patent
Shafer et al.

(10) Patent No.: US 10,292,587 B2
(45) Date of Patent: May 21, 2019

(54) ENERGY HARVESTER FOR WILDLIFE MONITOR

(71) Applicant: Arizona Board of Regents acting for and on behalf of Northern Arizona University, Flagstaff, AZ (US)

(72) Inventors: Michael W. Shafer, Flagstaff, AZ (US); Eric R. Morgan, Bolton, MA (US); Gregory Hahn, Flagstaff, AZ (US)

(73) Assignee: Arizona Board of Regents acting for and on behalf of Northern Arizona University, Flagstaff, AZ (US)

( * ) Notice: Subject to any disclaimer, the term of this patent is extended or adjusted under 35 U.S.C. 154(b) by 18 days.

(21) Appl. No.: 15/173,540

(22) Filed: Jun. 3, 2016

(65) Prior Publication Data
US 2016/0357238 A1    Dec. 8, 2016

Related U.S. Application Data

(60) Provisional application No. 62/171,927, filed on Jun. 5, 2015.

(51) Int. Cl.
*G06F 1/26* (2006.01)
*A61B 5/00* (2006.01)
(Continued)

(52) U.S. Cl.
CPC .......... *A61B 5/0022* (2013.01); *A01K 11/008* (2013.01); *A01K 61/90* (2017.01); *F03B 13/00* (2013.01); *G16H 40/67* (2018.01); *H02K 7/1823* (2013.01); *A61B 5/01* (2013.01); *A61B 2503/40* (2013.01); *A61B 2560/0214* (2013.01);
(Continued)

(58) Field of Classification Search
CPC .... A61B 5/0022; A01K 61/90; A01K 11/008; H02K 7/1823
See application file for complete search history.

(56) References Cited

U.S. PATENT DOCUMENTS 3,418,818 A    12/1968  Vincent et al.
3,436,914 A *  4/1969  Rosfelder ............... E21B 7/124
                                                        175/6

(Continued)

FOREIGN PATENT DOCUMENTS

CA          2467287 A1    11/2005

OTHER PUBLICATIONS

Michael W. Shafer et al., Abstract of "Energy Harvesting for Marine-Wildlife Monitoring," submitted to ASME Jun. 2, 2014 prior to ASME 2014 Conference on Smart Materials, Adaptive Structures and Intelligent Systems (ASME SMASIS 2014), Newport, Rhode Island.

*Primary Examiner* — Tulsidas C Patel
*Assistant Examiner* — Joseph Ortega
(74) *Attorney, Agent, or Firm* — IPTechLaw

(57) ABSTRACT

Implementations of energy harvester systems may include: an accumulator having an air bladder separated from water by a membrane; one or more hydro turbines coupled with the accumulator; two or more check valves each coupled with one of the one or more hydro turbines; a system battery coupled to the power conditioner; and an electronic load coupled to the system batter through the power conditioner; wherein the two or more check valves are configured to be in contact with water.

20 Claims, 11 Drawing Sheets

(51) Int. Cl.
*A01K 11/00* (2006.01)
*A01K 61/00* (2017.01)
*F01D 15/10* (2006.01)
*H02K 7/18* (2006.01)
*A01K 61/90* (2017.01)
*F03B 13/00* (2006.01)
*G16H 40/67* (2018.01)
*A61B 5/01* (2006.01)

(52) U.S. Cl.
CPC ..... *F05B 2220/602* (2013.01); *F05B 2250/82* (2013.01); *F05B 2260/42* (2013.01); *Y02B 10/50* (2013.01); *Y02P 60/64* (2015.11)

(56) References Cited

U.S. PATENT DOCUMENTS

| | | | |
|---|---|---|---|
| 3,504,648 A | 4/1970 | Kriedt | |
| 4,392,063 A * | 7/1983 | Lindquist | F03B 11/02 290/52 |
| 4,555,637 A * | 11/1985 | Irvine | F01D 15/10 290/52 |
| 4,731,545 A * | 3/1988 | Lerner | H02K 7/1823 290/43 |
| 4,740,711 A * | 4/1988 | Sato | F01B 13/061 290/52 |
| 5,494,468 A | 2/1996 | Demarco, Jr. | |
| 6,109,029 A * | 8/2000 | Vowles | B01D 61/10 270/42 |
| 6,745,069 B2 | 6/2004 | Nissila et al. | |
| 6,755,797 B1 | 6/2004 | Stouffer | |
| 7,249,805 B2 | 7/2007 | Cap | |
| 7,636,051 B2 * | 12/2009 | Imai | H04L 43/0817 340/500 |
| 7,724,145 B2 | 5/2010 | Batra et al. | |
| 7,832,979 B2 * | 11/2010 | Yaras | F03B 17/06 415/4.3 |
| 8,193,655 B2 | 6/2012 | Roberts et al. | |
| 8,359,172 B2 | 1/2013 | Fattah | |
| 8,476,778 B2 | 7/2013 | Weinberger et al. | |
| 8,717,165 B2 | 5/2014 | Gernandt et al. | |
| 9,606,220 B2 * | 3/2017 | Berumen | A01K 11/006 |
| 9,618,002 B1 * | 4/2017 | Cabra | F03B 13/00 |
| 10,084,313 B2 * | 9/2018 | Berkcan | H02J 3/00 |
| 2002/0070554 A1 * | 6/2002 | Anderson | F02B 63/04 290/1 R |
| 2003/0168861 A1 | 9/2003 | Estevez | |
| 2007/0285053 A1 * | 12/2007 | Noguchi | H02J 7/32 320/114 |
| 2008/0284174 A1 * | 11/2008 | Nagler | F03B 13/00 290/54 |
| 2010/0270803 A1 * | 10/2010 | Irwin | F03B 3/02 290/54 |
| 2011/0006532 A1 * | 1/2011 | Grey | F03B 13/148 290/53 |
| 2011/0304144 A1 * | 12/2011 | Dehlsen | E02B 9/08 290/53 |
| 2012/0028538 A1 * | 2/2012 | Wong | H02J 7/32 446/457 |
| 2012/0137950 A1 | 6/2012 | Rapp et al. | |
| 2012/0187693 A1 * | 7/2012 | Houvener | F03B 17/061 290/54 |
| 2012/0266590 A1 | 10/2012 | Janes et al. | |
| 2012/0289103 A1 | 11/2012 | Hudson et al. | |
| 2013/0181839 A1 | 7/2013 | Cao | |
| 2013/0207815 A1 | 8/2013 | Pitchford et al. | |
| 2015/0345260 A1 * | 12/2015 | Green | E21B 41/0085 310/68 R |
| 2016/0376910 A1 * | 12/2016 | Sellers | F03D 1/04 290/52 |
| 2018/0082166 A1 * | 3/2018 | Kukulya | G01S 7/521 |

* cited by examiner

ENERGY HARVESTER FOR WILDLIFE MONITOR

CROSS REFERENCE TO RELATED APPLICATIONS

This document claims the benefit of the filing date of U.S. Provisional Patent Application 62/171,927, entitled "Energy Harvester for Marine Wildlife Monitor" to Michael W. Shafer, Eric Morgan and Gregory Hahn which was filed on Jun. 5, 2015, the disclosure of which is hereby incorporated entirely herein by reference.

STATEMENT REGARDING FEDERALLY SPONSORED RESEARCH OR DEVELOPMENT

This invention was supported by the United States Government under National Science Foundation Grant No. 1537203. The Government has certain rights in the invention.

BACKGROUND

1. Technical Field

Aspects of this document relate generally to powering biological monitors, such as wildlife tracking tags. More specific implementations involve biomechanical energy harvesters.

2. Background

Conventionally, to gather information about wild animals electronic tagging systems are used. The monitors need a power supply to gather and transmit energy for an extended period of time. Conventional power sources for the monitors include rechargeable and non-rechargeable batteries.

SUMMARY

Implementations of energy harvester systems may include: an accumulator having an energy storage system separated from water by a membrane; one or more hydro turbines coupled with the accumulator; two or more check valves each coupled with one of the one or more hydro turbines; a system battery coupled to the power conditioner; and an electronic load coupled to the system battery through the power conditioner; wherein the two or more check valves are configured to be in contact with water.

Implementations of energy harvester systems may include one, all, or any of the following:

The energy storage system includes an air bladder separated from the water by a membrane.

The energy storage system is a spring coupled to the membrane, wherein the membrane is configured to bias the spring in response to pressure force.

The energy harvester system may further include a secondary fluid reservoir coupled to an inlet and an outlet of the system, the secondary fluid reservoir may include a working fluid separated from the water by a second membrane, wherein compression of the working fluid occurs in response to pressure force thereby storing energy in the energy storage system.

The working fluid may be one of fresh water or oil.

The energy harvester system may further include a second hydro turbine coupled with a second check valve.

The electronic load may include monitoring and communication equipment.

The system may be coupled to a bio-logger configured to be coupled to an animal.

The system may be coupled to a telemetry tag configured to be coupled to an animal.

Implementations of energy harvester systems may include: a first hydro turbine and a second hydro turbine, each turbine having an inlet and an outlet; a pressure accumulator having an energy storage system and a fluid section separated by a membrane, the pressure accumulator coupled with the outlet of the first hydro turbine and the inlet of the second hydro turbine; a first high-hysteresis check valve, coupled to the inlet of the first hydro turbine; a second high-hysteresis check valve, coupled to the outlet of the second hydro turbine; a power conditioner electrically coupled to the first and to the second hydro turbine; a system battery electrically coupled with the power conditioner; and an electronic load electrically coupled with the system batter through the power conditioner. The first hydro turbine and the second hydro turbine may be configured to generate electricity and charge the system battery when water flows into the first hysteresis check valve through the first hydro turbine and when water flows through the second hysteresis check valve from the pressure accumulator and through the second hydro turbine.

Implementations of energy harvester systems may include one, all, or any of the following:

The energy storage system may include one or more springs and the membrane may be configured to bias the one or more springs in response to pressure force.

The energy storage system may include an air bladder.

The energy harvesting system may further include a secondary fluid reservoir coupled to an inlet and an outlet of the system, the secondary fluid reservoir comprising a working fluid separated from the water by a second membrane, wherein compression of the working fluid occurs in response to pressure force, storing energy in the energy storage system.

The working fluid may be one of water or oil.

The electronic load may include monitoring and communication equipment.

The system may be coupled to a bio-logger configured to be coupled to an animal.

The system may be coupled to a telemetry tag configured to be coupled to an animal.

Implementations of methods for powering an animal monitor may include: receiving water at a high hysteresis check valve wherein the water is moved by pressure force; receiving the water at an inlet of a first hydro turbine coupled with the check valve; generating electricity for a system battery using the first hydro turbine and the water; receiving the water into the pressure accumulator and increasing a pressure of the pressure accumulator, the pressure accumulator coupled with the first hydro turbine; receiving water at an inlet of a second hydro turbine from the pressure accumulator, the water moving under pressure force; generating electricity for the system battery using the second hydro turbine and the water; receiving at a second high-hysteresis valve the water from the second hydro turbine; and releasing the water through the second check valve; wherein the system battery powers a monitor configured to be coupled to an animal.

Implementations of a method for powering an animal monitor may include one, all, or any of the following:

The monitor may be a telemetry tag.

The monitor may be a bio-logger.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components, assembly procedures or method elements disclosed herein. Many additional components, assembly procedures and/or method elements known in the art consistent with the intended energy harvesting systems and methods for powering an animal monitor will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such energy harvesting systems and methods for powering an animal monitor and implementing components and methods, consistent with the intended operation and methods.

Figure 1:
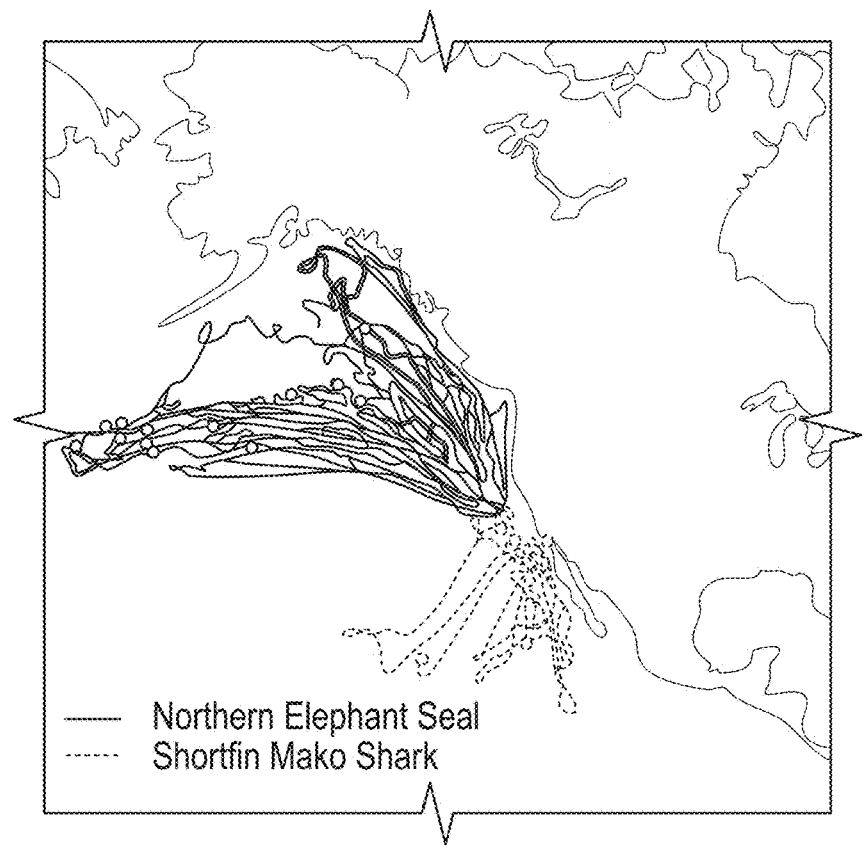
FIG. 1 is a plan view of the tracking data for two marine animals.

Referring now to FIG. 1, data collected from a marine wildlife monitor (monitor) is illustrated. Monitors are used for a variety of purposes such as tracking the geographic regions and movements of animals. Monitors may also be referred to as tags or bio-loggers. In FIG. 1, the movement of at least one northern elephant seal and at least one shortfin mako shark is illustrated. The movement of the animals is along the western coast of North America. The animals' movements are mostly in separate geographic locations but their movement does overlap off the coast of California. Movements such as these may be tracked using a global positioning system (GPS) with the assistance of satellites and/or triangulation using earth-based beacons or the like. The data illustrated in FIG. 1 is two dimensional (2D), however some monitors can also monitor depth movements as will be described hereafter.

Figure 2:
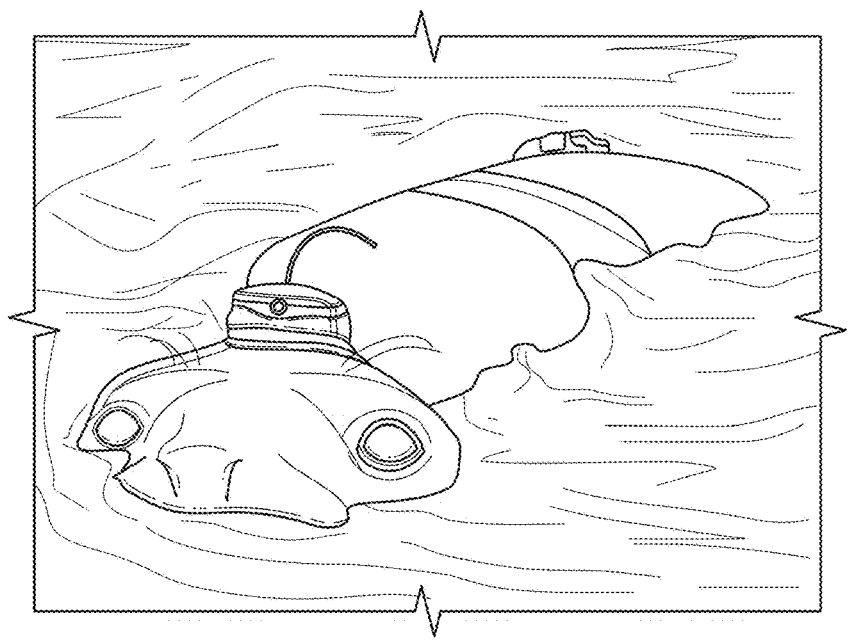
FIG. 2 is a front view of a conventional monitor (tag) device positioned on an animal.

Monitors may in various implementations be used to capture data about the animal to which they are attached and/or they may be used to capture data about the environment in which the marine animal is located. Some monitors are only configured to capture environmental data and not data about the animal. These monitors simply use the animal as a carrier for the device. Further details about existing monitors are described in, "Hydrostatic pressure-cycle energy harvester," Shafer, Michael W., Hahn, Gregory and Morgan, Eric, SPIE Proceedings Vol. 9431: Active and Passive Smart Structures and Integrated Systems 2015, April 2015; and "Energy Harvesting for Marine-Wildlife Monitoring," Shafer, Michael W. and Morgan, Eric, Proceedings of the AMSE 2014 Conference on Smart Material, Adaptive Structures and Intelligent Systems, September 2014, which are hereby incorporated entirely herein by reference Referring now to FIG. 2, an implementation of a monitor coupled to the head of a marine animal is illustrated. In order to capture data, the monitor must be at least temporarily attached to a marine animal. Monitors may be attached to various portions of an animal's body such as the head, the fins, the tail, and so forth. Because the animal is generally in movement and not stationary, manual retrieval of the monitor is inconvenient and/or costly. Accordingly, various mechanisms have been used to retrieve the data collected by the monitors. In some cases, the monitor collects data and then, at a predetermined time, detaches from the host animal and floats to the surface. It may then be retrieved. Such monitors may emit signals when detached so as to be more easily retrieved.

Other monitors stay attached to the animal but regularly transmit data such as through satellite transmissions. As such, transmissions are difficult or impossible when the animal is at deeper depths, so the monitors generally are configured to, at the time the animal surfaces, quickly capture a GPS coordinate of the animal and/or transmit this and other collected data via satellite. In this way the incremental movements and other data of an animal may be monitored in something closer to real time than is the case with a monitor whose data is not accessible until physically retrieved.

Figure 3:
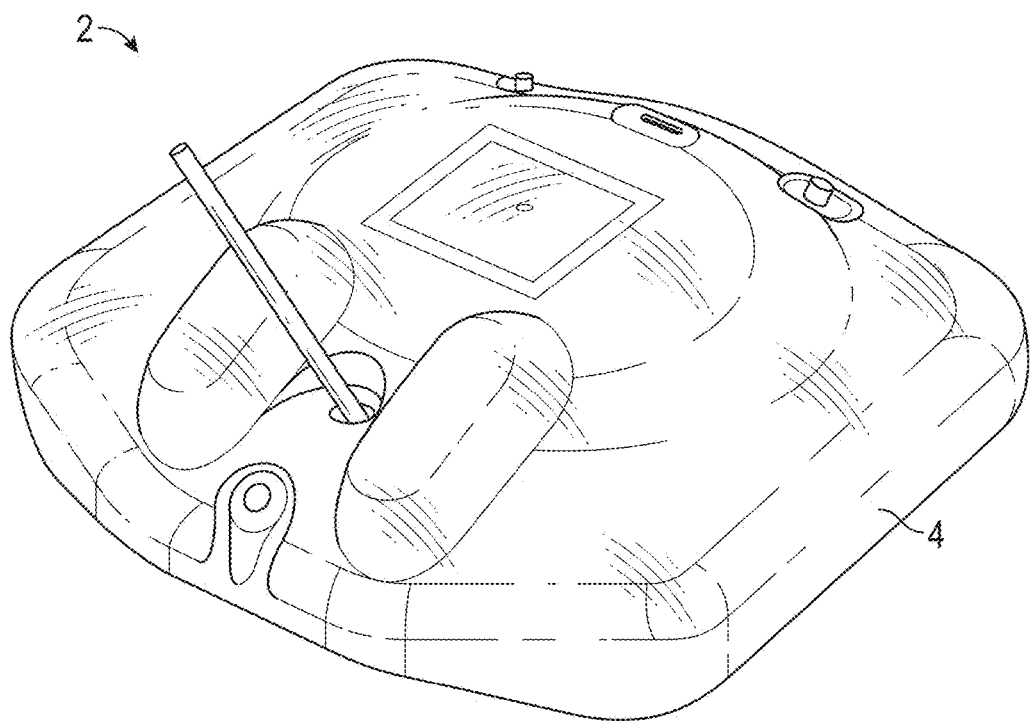
FIG. 3 is a perspective view of a conventional monitor (tag) device.
Figure 4:
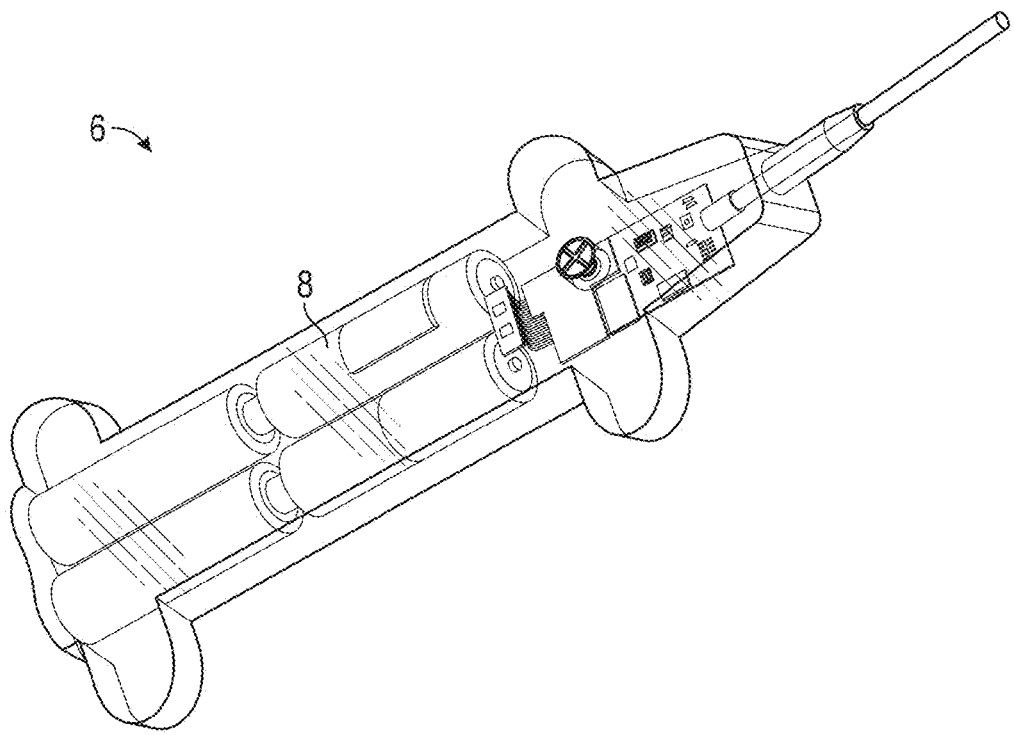
FIG. 4 is a perspective view of another conventional monitor (tag) device.

Naturally, monitors of this nature must be powered by some means or another. Various powering methods have been used, some with more success than others. Batteries are a commonly used power source for such monitors. Referring to FIG. 3, the monitor 2 illustrated is a SPLASH10-296F model manufactured by Wildlife Computers of Redmond, Wash. The monitor 2 is used to record temperature, depth and light level when attached to an adult hard-shell sea turtle. This monitor 2 uses at least four batteries 4 that extend across the width of the monitor 2. Referring to FIG. 4, the monitor 6 illustrated is a temperature monitor for attachment to a penguin, model SPOT-275 manufactured by Wildlife Computers of Redmond, Wash. This monitor 6 is powered using four batteries 8. As can be seen in FIGS. 3 and 4, batteries generally take up most of the volume of the device and in some cases batteries take up significantly more volume than the circuitry and electronics which are used to capture, store and transmit the data. The larger a device, the more drag may be created on the animal. It has been observed that as the drag increases the likelihood of detachment increases as well. Accordingly, while batteries can be used, simply using more batteries or larger batteries for longer device life is not necessarily a viable option because such devices may more likely detach and once detached, the device is no longer providing effective monitoring of the animal or environment.

Figure 6:
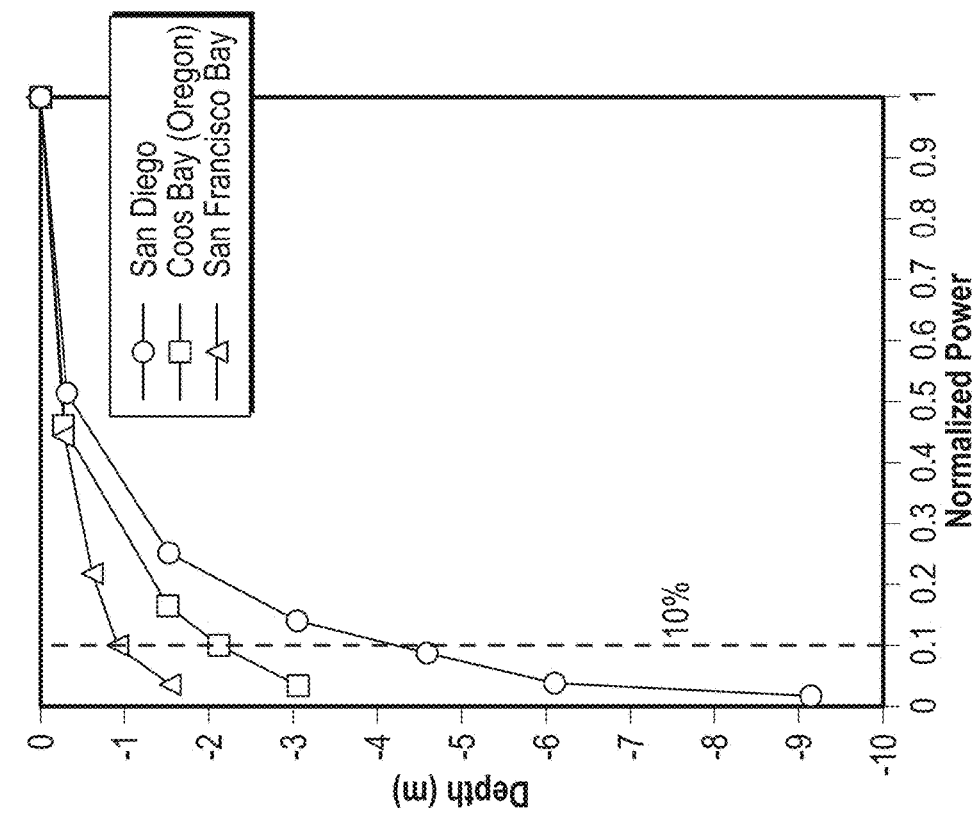
FIG. 6 is a graph comparing normalized power based on ocean depths through photovoltaic cells at different locations.
Figure 5:
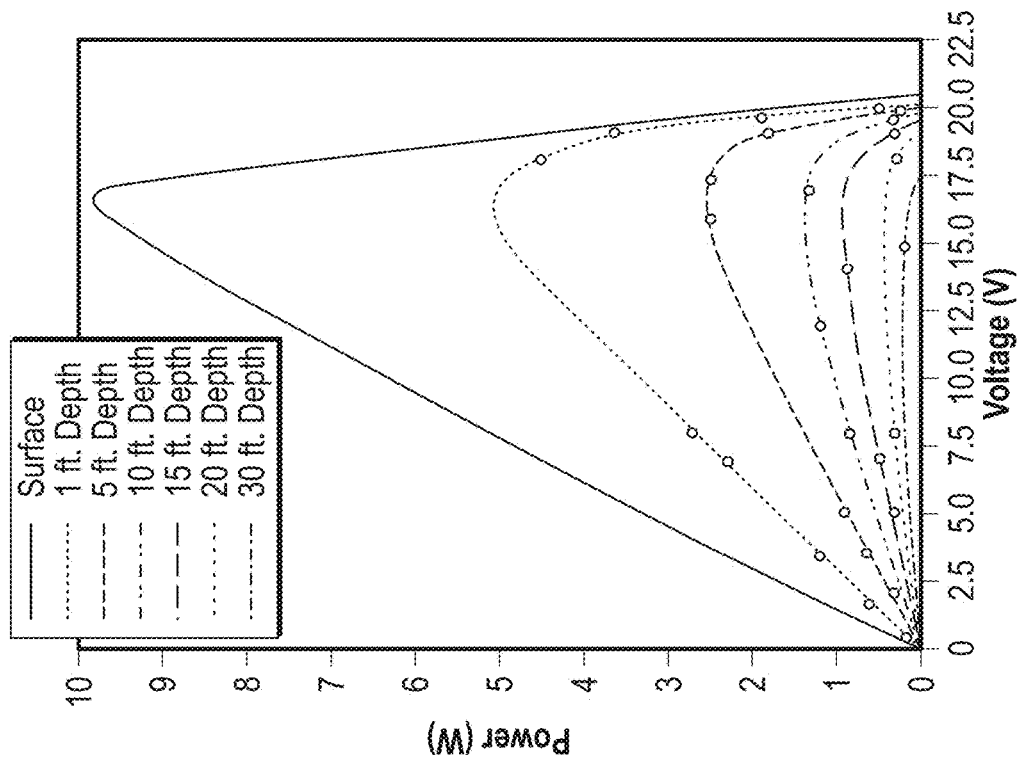
FIG. 5 is a graph of solar cell power outlet at different depths.

Attempts have been made to use rechargeable devices, such as those that are recharged through photovoltaic means. This is a more likely option for marine animals that spend large amounts of time on land or that spend large amounts of time near the surface of the water. Referring to FIG. 5, the light available to a solar cell dramatically decreases as an animal dives to deeper depths. The graph shown in FIG. 5 represents the Pacific Ocean at San Diego, Calif. The profile varies by oceanic location but, in general, the outcome is the same—when the animal is deeper there is very little light available to a solar cell. For Example, FIG. 6 shows that, for one solar powered device, the device is only at 10% of normalized power at a depth of only about 1 meter below the surface of San Francisco Bay, or about 2 meters below the surface at Coos Bay near Oregon, or about 4.5 meters below the surface of San Diego Bay.

Accordingly, attempting to use photovoltaic methods to recharge a power source for a monitor is not nearly as useful or viable for animals that spend much of their time one or more meters below the surface of the water. For example, in Table 1 below several monitors and their various characteristics are shown, including: Type (brand name) of monitor; Capabilities (data collected and mounting position on animal); Model number; Life span of the tag; Stored Battery Energy; and Daily Energy Budget. In the "Capabilities" column it is indicated that position data is generally gathered and/or transmitted using the ARGOS and/or GPS satellite systems for such monitors.

TABLE 1

| Type | Capabilities | Model Number | Lifespan (days) | Stored Battery Energy (kJ) | Daily Energy Budget (J/day) |
|---|---|---|---|---|---|
| SPOT5 | ARGOS, | 203I | 1240 | 145.3 | 117 |
| | Position, | 275A | 120 | 16.1 | 135 |
| | Backmount | 287C | 400 | 48.4 | 121 |
| | ARGOS, | 182C | 220 | 24.2 | 110 |
| | Position, | 196F | 220 | 32.3 | 147 |
| | Finmount | 257A | 980 | 113.0 | 115 |
| | | 258A | 220 | 32.3 | 147 |
| SPLASH10 | ARGOS, | 280A | 300 | 80.7 | 269 |
| | Position, | 283B | 180 | 48.4 | 269 |

TABLE 1-continued

| Type | Capabilities | Model Number | Lifespan (days) | Stored Battery Energy (kJ) | Daily Energy Budget (J/day) |
|---|---|---|---|---|---|
| | Sensor Data, Backmount | 309A | 180 | 48.4 | 269 |
| | ARGOS, | 268C | 100 | 32.3 | 323 |
| | Position, | 289A | 200 | 48.4 | 242 |
| | Sensor Data, | 312A | 100 | 32.3 | 323 |
| | Finmount | 316A | 100 | 32.3 | 323 |
| SPLASH10-F | GPS | 238A | 460 | 129.2 | 281 |
| | Position, | 238D | 460 | 129.2 | 281 |
| | Sensor Data, | 296A | 460 | 129.2 | 281 |
| | Finmount | 297A | 240 | 48.4 | 202 |

Table 1 shows that, while different systems vary in their daily energy usage, the least amount of energy expended per day for the monitors shown is 110 Joules (J) for the SPOTS model 182C and the most amount of energy expended per day for the monitors shown in the table is 323 J for the SPLASH model 268C. Monitors that capture more data, or capture it more frequently, or communicate it more frequently through satellite systems, or otherwise perform more complicated or frequent processes, expend more energy per day. It should be noted that these tags use between 100-350 J/day.

Figure 7A:
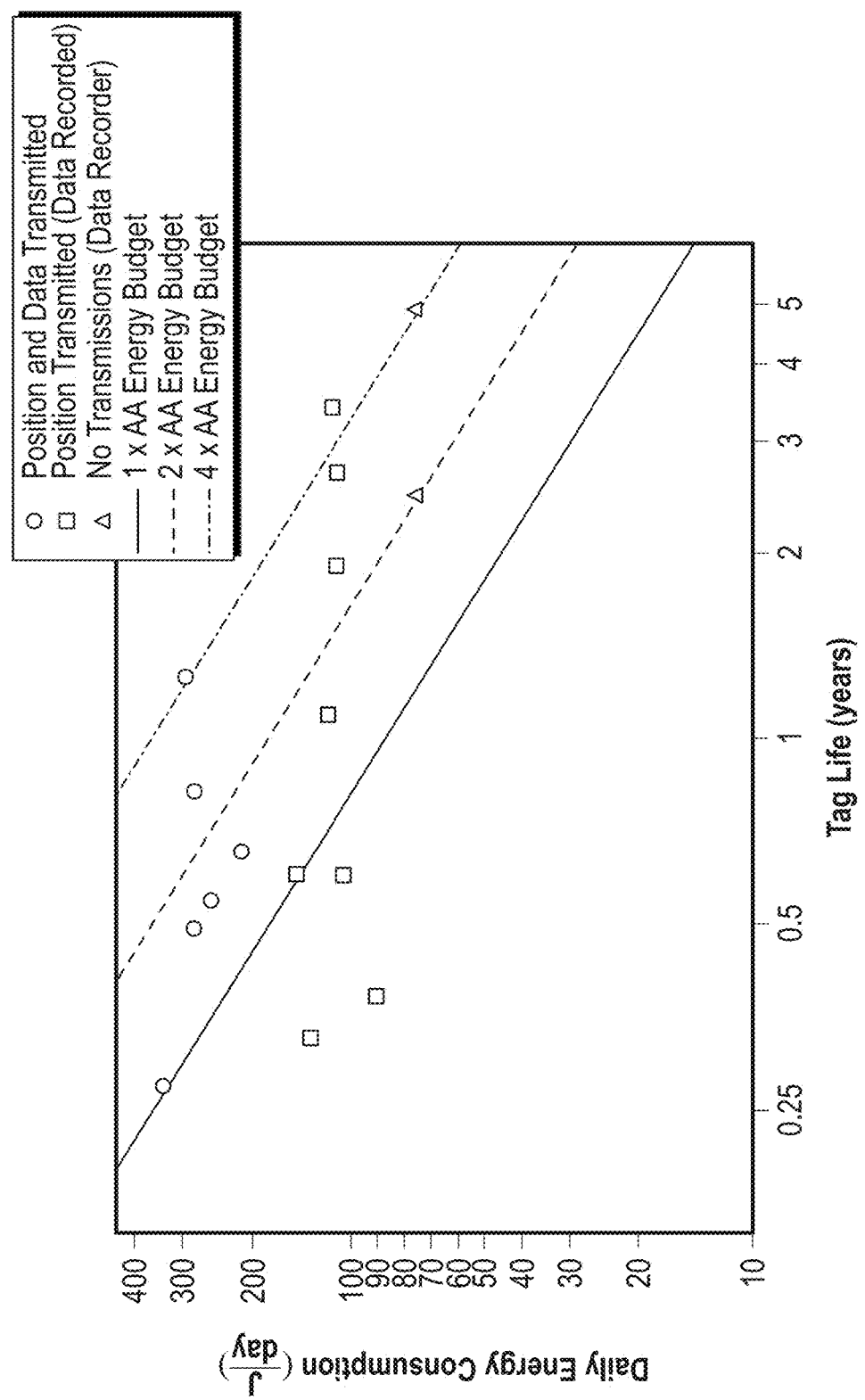
FIG. 7A is a graph comparing the daily energy consumption of animal monitoring tags to the life of the tag.

Referring now to FIG. 7A, a graph is given that shows daily energy consumption plotted against tag (monitor) life in years. As is expected, those monitors with increased capabilities use more daily energy and have a shorted tag life. Lines are given which show the number of batteries a unit would/does require, i.e., 1AA battery, 2AA batteries or 4AA batteries. This figure graphically presents the data from Table 1 wherein the maximum daily usage is on the order of 300 J/day.

Figure 8:
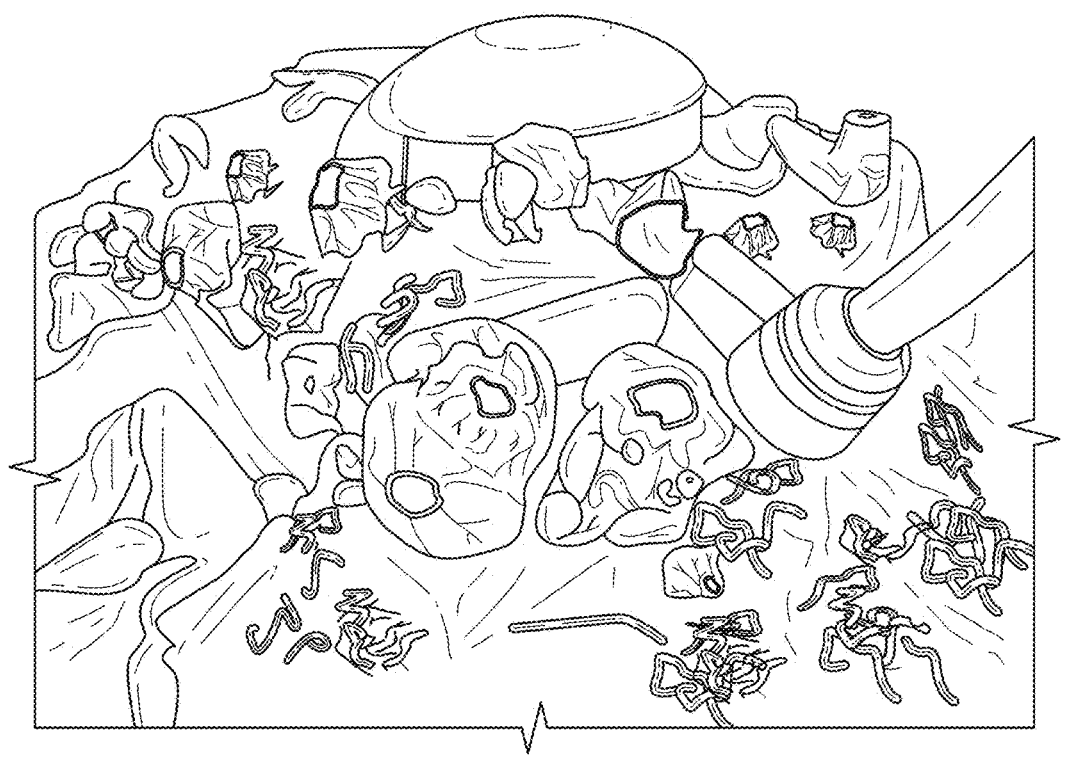
FIG. 8 is a drawing of bio-fouling on a tag.

Various implementations of charging systems for wildlife monitors are disclosed in this document. These implementations do not rely on solar energy. Also, the systems disclosed may be less likely to be hindered by bio-fouling such as plant, bacteria, virus, animal, and other growth on the device. Referring to FIG. 8, a monitor covered in bio-fouling is illustrated. Bio-fouling of the monitor can also injure or molest the animal and/or cause the device to become detached therefrom.

Figure 9:
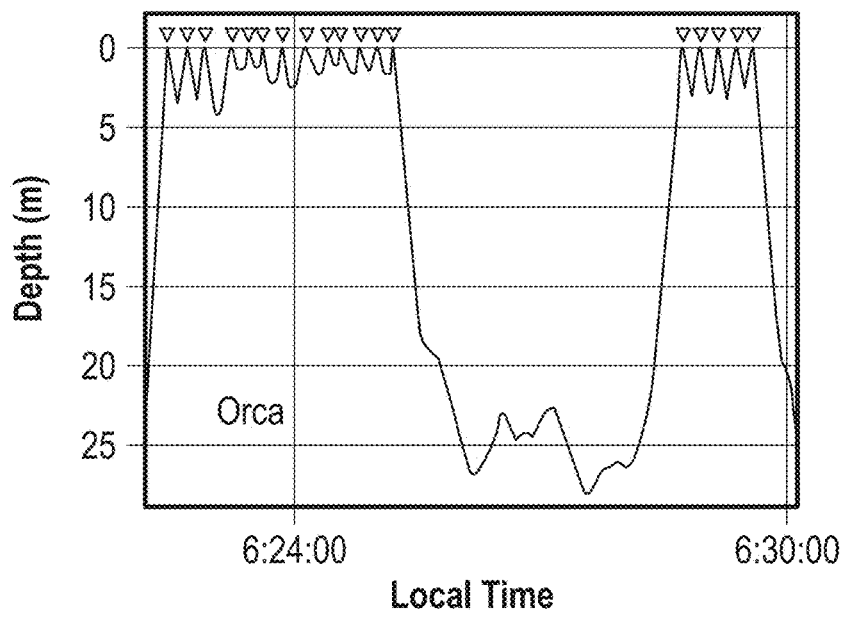
FIG. 9 is a graph depicting the dive patterns of an Orca.
Figure 10:
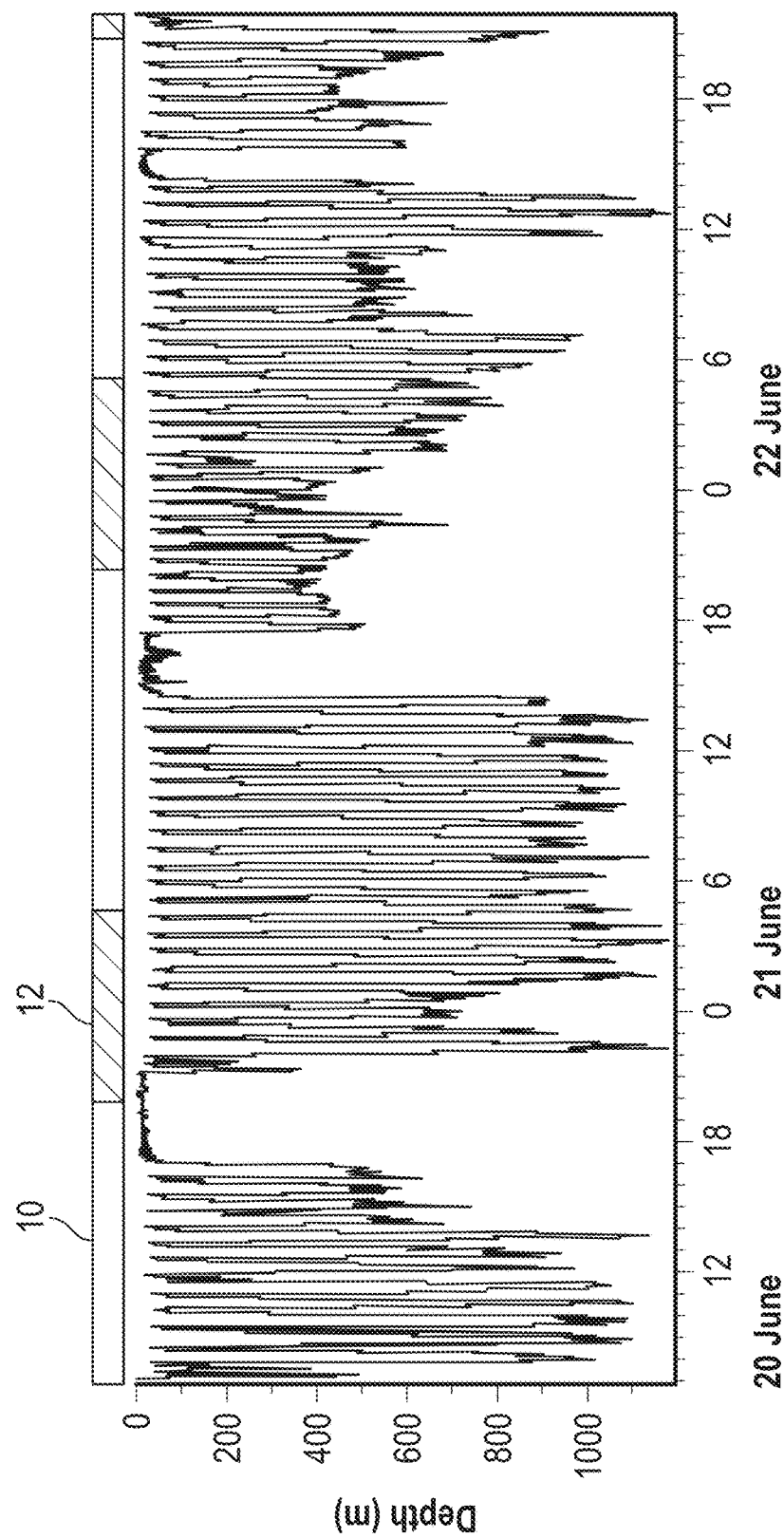
FIG. 10 is a graph depicting the dive patterns of a sperm whale.
Figure 11:
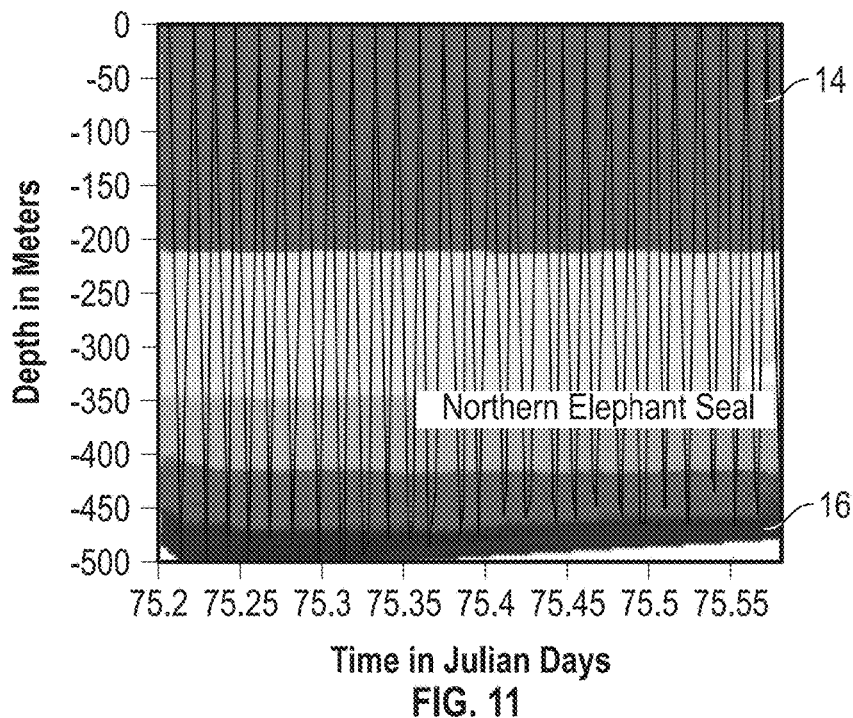
FIG. 11 is a graph depicting the diver patterns of a Northern Elephant Seal.

Referring to FIG. 9-11, graphs of the dive patterns of marine animals are illustrated. Many marine animals dive regularly throughout the day anywhere from tens to hundreds of meters (or more than 1 kilometer (km)) below the surface of the water. FIG. 9, represents the diving characteristics of an orca, showing periods of many, relatively, shallow dives of less than 5 meters below the surface, each ending in a breathing event (represented by a triangle), following by a deeper diving event (to about 25 meters) and lasting a few minutes, followed again by a series of shallow dives and respiration events, and then another deeper dive. This data was collected by a monitor that tracked depth of an orca versus time.

Referring to FIG. 10, a graph illustrating a diving profile for a sperm whale is shown. Each tick mark on the lower horizontal axis represents one hour. On top of the graph, the white bars 10 represent daytime hours and the cross-hatched bars 12 represent nighttime hours. The graph reveals alternating periods of shorter dives closer to the surface followed by periods of repeated deeper dives (around 20-30 in number) to depths ranging from about 400 to 1200 meters. The monitor used in this case tracked the depth of the whale as a function of time.

Referring to FIG. 11, a graph is shown revealing the diving profile for a northern elephant seal plotting depth as a function of time. The shaded portions of the graph demonstrate the change in temperature as the northern elephant seal dives. The upper 14 dark portion of the graph is warmer water while the lower 16 dark portion is much cooler water. The monitor on this animal gathered data related to depth as a function of time and temperature as a function of depth. The behavior of the northern elephant seal over the time period is seen to be a regular series of repeated dives to depths of about 400-500 meters.

There are many marine animals which regularly dive throughout the day. Referring to Table 2 below, various species and their daily dive frequency, mean dive duration, mean dive depth and average speed are shown. Some powering mechanisms utilize water flow, which may be based (or whose energy recharging capabilities are calculated) in part on the average speed of a marine animal. Other powering mechanisms may be based (or whose energy recharging capabilities are calculated) on the dive characteristics of an animal. Both types of powering mechanisms are further explained in the above referenced publications previously incorporated by reference.

TABLE 2

| Species | Dive Frequency (dives/day) | Mean Dive Duration (min) | Mean Dive Depth (m) | Average Speed (m/s) |
|---|---|---|---|---|
| Northern elephant seal | 60 | 22 | 428 | 0.9-1.6 |
| Yellowfin tuna | 20.2 | 2-10 | 50-300 | 0.46-0.9 |
| Sperm Whale | 29 | 36.2 | 800 | 0.8 |
| Orca (shallow/respirating) | 600-756 | 0.38-0.55 | 2.75 | 1.6 |
| Orca (deep/hunting) | 66-102 | 4.25-4.75 | 29 | |
| Leatherback sea turtle | 84-120 | 10 | 61.6 | 0.9 |

Because water pressure varies at different depths, and because many water-inhabiting animals repeatedly dive during the day, it is possible to construct an energy harvesting system for monitors which harvests energy from repeated pressure differences. In Table 3 below, for example, calculations based on several assumptions are provided. Using the average number of dives per day for the five marine animals listed in the first column, assuming a displaced volume of 250 cubic centimeters (cc) (which is about 1 cup), and assuming one harvesting cycle per dive, the energy/day is given in kJ. As seen in the fifth column, the lowest calculated energy per day is 8.9 kJ (well above the maximum value of about 100-350 J used daily by many monitors, as discussed above). Then, assuming a target energy/day of 200 J, the sixth column calculated the required efficiencies of such systems. As can be seen, the required transduction efficiencies range between 0.31% to 2.2% efficiency. These ranges are possible using existing equipment and/or with feasible modifications as described in the above referenced publications and herein.

TABLE 3

| Species | Depth (m) | Pressure at depth (atm) | Energy (J) | Energy/ day (kJ/day) | Required Efficiency (%) |
|---|---|---|---|---|---|
| Northern elephant seal | 428 | 43 | 1080 | 65 | 0.31 |
| Yellowfin tuna | 175 | 17 | 440 | 8.9 | 2.2 |
| Sperm whale | 800 | 80 | 2020 | 59 | 0.34 |
| Orca | 2.75/29 | 0.3/3 | 7/73 | 11 | 1.8 |
| Leatherback sea turtle | 29 | 6.2 | 160 | 16 | 1.3 |

Figure 12:
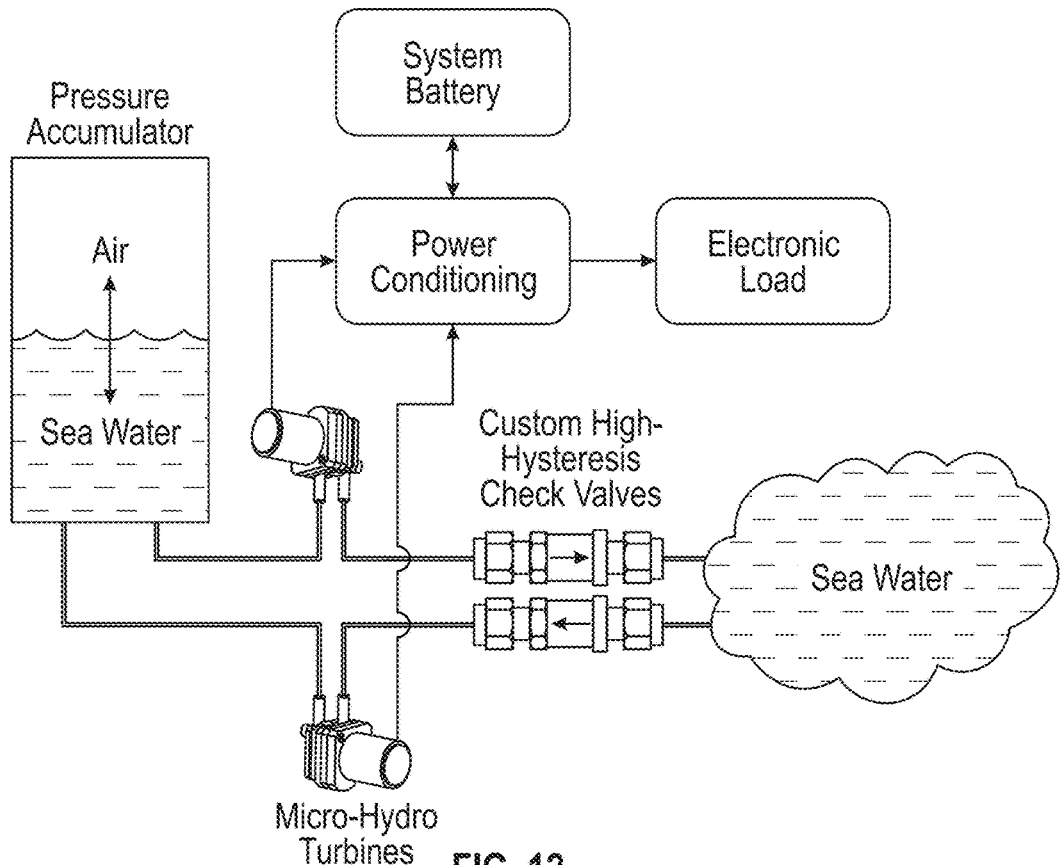
FIG. 12 is block diagram representation of an implementation of an energy harvesting system.

Referring to FIG. 12, an implementation of an energy harvesting system is illustrated. While the above table assumes only one harvesting cycle per dive, the implementation in FIG. 12 may have two harvesting cycles per dive. The system has an accumulator having an air bladder separated from seawater by a membrane. The accumulator is coupled with a pair of hydro turbines, which, in some implementations, may be micro-hydro turbines. Each micro-hydro turbine is coupled with a high-hysteresis check valve. The check valves are configured to be in contact with the surrounding seawater. When a marine animal dives and reaches a predetermined water pressure, the first check valve opens and the water is moved by a pressure force until the pressure in the pressure accumulator is equal to the seawater pressure. The water flow during this process turns the first hydro turbine to produce electricity which is then stored by the system battery through a power conditioner and other elements, thus charging the system battery. The air in the pressure accumulator compresses as the seawater enters the accumulator to equalize the pressure. Once the pressure is equalized, the first check valve closes. Instead of the On the up cycle, as the animal ascends back towards the surface of the water, when the animal reaches a predetermined lower pressure depth, the second check valve opens and water is moved through pressure force out from the accumulator into the surrounding seawater until the pressure in the pressure accumulator and the surrounding seawater are equalized. The water flow during this stage turns the second hydro turbine which charges the system battery as described above for the first hydro turbine. When the pressure in the accumulator and surrounding seawater are equalized the second check valve closes. This cycle may be repeated each time the animal traverses the upper depth and lower depth, and vice versa, needed to operate the check valves.

The system battery is then used to operate the electronic load, which includes the monitoring equipment which gathers data and reports it through satellite means and the like. The battery is shown as being coupled to the electronic load through power conditioning circuitry and the like. This coupling may be necessary to provide proper voltage and the like to the electronic load. As may be understood, system implementations like those disclosed herein may hypothetically have an indefinite life, or at the very least, a life which last orders of magnitude longer than existing monitors. The life of this system may be limited by other things, such as the life of a rechargeable battery, the ability of the check valves to remain free of bio-fouling so they remain operational, the life of the hydro turbines, the life of the electronic circuitry and so forth. All these considered, it is believed the life of monitors employing such implementations of energy harvesting systems as those disclosed herein would be greatly enlarged over existing monitor systems.

Alternate configurations of this system could be developed that would implement a single valve and hydro-turbine/generator in order to simplify the operational complexity and number of components of the system. Additionally, the system can be made to be sealed from outside seawater to eliminate biofouling or otherwise within the workings of the device. In this implementation, a secondary fluid reservoir similar to the pressure accumulator would be connected to the inlet and outlet of the system shown in FIG. 12. This secondary fluid reservoir would contain and separate the working fluid of the hydro system (water, oil, etc.) from the outside seawater by a flexible membrane or moving surface in the same way that the pressure accumulator separates air from seawater in FIG. 12. In FIG. 12 however, seawater is shown as the working fluid, whereas in a sealed configuration, the working fluid may be fresh water, oil, etc. When configured in this way, the system could transfer the seawater pressure to the working fluid of the system without direct contact of the seawater and it contaminants with the inner workings of the device. Other implementation of the pressure accumulator may include one or more springs. The membrane of the pressure accumulator may be configured to compress the springs when the pressure of the system increases. The potential energy of the compressed springs may be used to push the water or working fluid through the hydro-turbine/generator.

Figure 13:
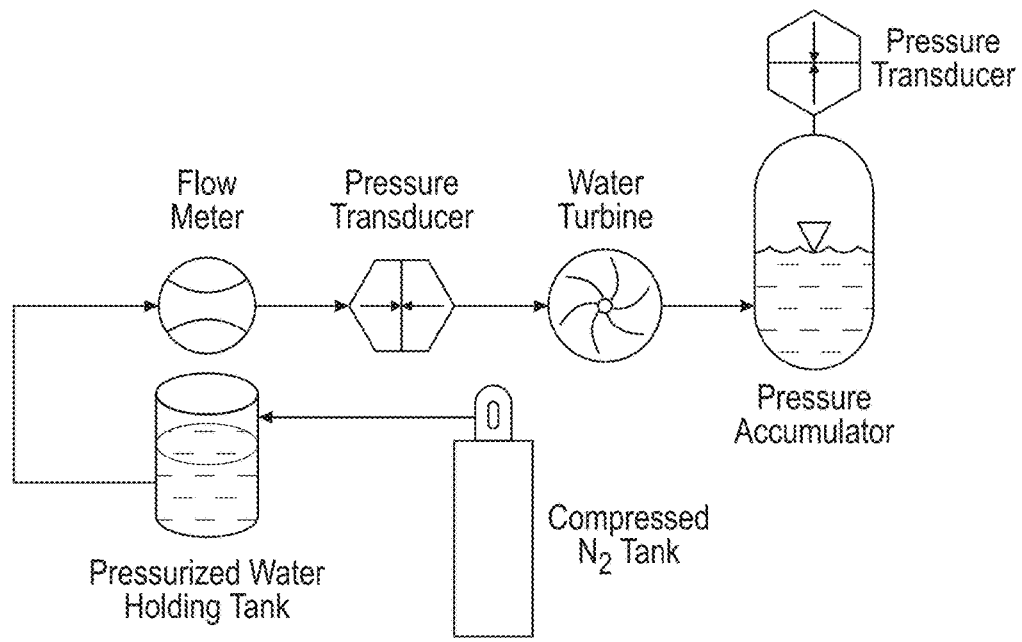
FIG. 13 is a schematic of an another implementation of an energy harvesting system.

Referring to FIG. 13, an implementation of an energy harvesting system is illustrated, which was used to demonstrate proof of concept. A pressured water holding tank was filled partially with water and was coupled with a compressed nitrogen ($N_2$) tank to simulate increased pressure at a lower water depth. Pressure transducers were placed at two locations to measure pressure, and a hydro turbine was coupled between the holding tank and a pressure accumulator, similar to the accumulator described in FIG. 12. The hydro turbine used in this implementation was an existing water pump used in reverse, the M200 pump manufactured by TCS Micropumps. This implementation was only run in the high pressure mode (i.e., the inlet cycle during higher water pressure outside the system).

In Table 4, below, various data for tests run using the M200 pump is given. In the tests conducted the pressure differences ranged from 50 to 100 pounds per square inch (psi) in increments of 10 psi. Representative water depths at these pressures are shown in the second column (for reference the depth as 90 psi is about 60 meters), and the electronic load was a 10 ohm load. The energy stored from adiabatic compression is given in the third column and the average voltage and total energy generated are given in the fourth and fifth columns, respectively. The efficiency is the total generated energy divided by the total stored energy and is given in the sixth column. From the test, it is shown that the efficiency ranges from 0.98% to 1.51% across input pressures tested. It is noted that most of the calculated required efficiencies of Table 3 are within or below this range.

TABLE 4

| Pressure Tested (PSI) | Equivalent depth (ft) | Energy Stored from Adiabatic Compression (J) | Average Voltage (V) | Total Energy Generated (J) | Efficiency |
| --- | --- | --- | --- | --- | --- |
| 100 | 194.586 | 59.575 | 0.9023 | 0.8999 | 1.51% |
| 90 | 171.828 | 56.692 | 0.8212 | 0.7827 | 1.38% |
| 80 | 149.069 | 53.468 | 0.7329 | 0.6785 | 1.27% |
| 70 | 126.310 | 49.813 | 0.6700 | 0.5722 | 1.15% |

TABLE 4-continued

| Pressure Tested (PSI) | Equivalent depth (ft) | Energy Stored from Adiabatic Compression (J) | Average Voltage (V) | Total Energy Generated (J) | Efficiency |
| --- | --- | --- | --- | --- | --- |
| 60 | 103.552 | 45.594 | 0.5936 | 0.4757 | 1.04% |
| 50 | 80.793 | 40.604 | 0.5132 | 0.3982 | 0.98% |

Figure 14:
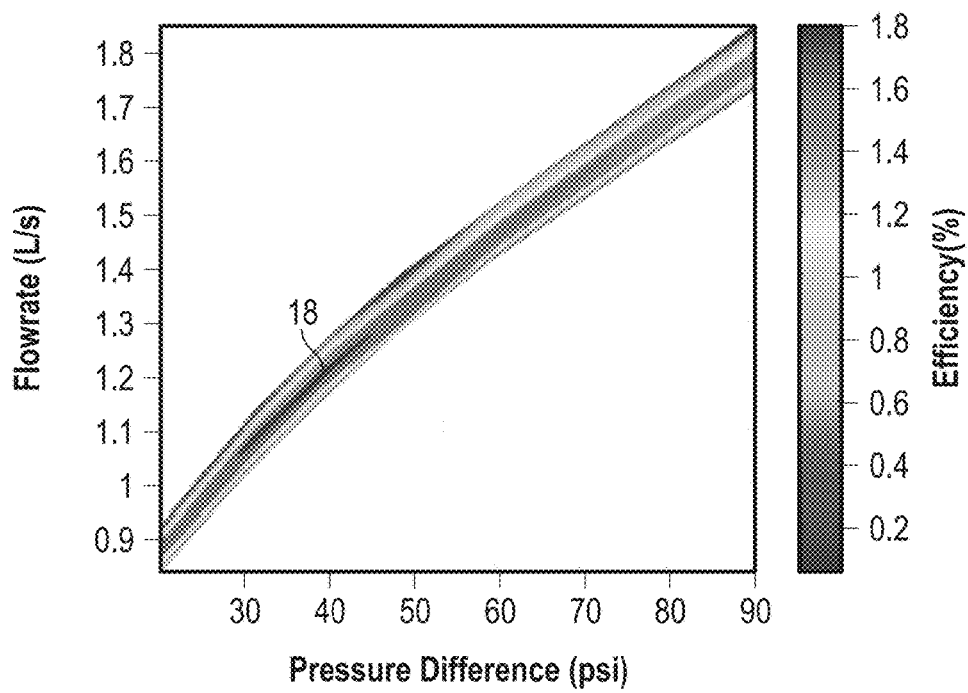
FIG. 14 is a graph depicting the relationship between flowrate and pressure difference in a turbine used in an implementation of an energy harvesting system.

Referring to FIG. 14, a graph showing the flowrate versus pressure difference of the system is illustrated. The flowrate is plotted in liters per second (L/s) against the pressure difference in psi. The efficiency percentage is also plotted, and it is seen that the flowrate at any given pressure difference can be optimized to achieve high efficiencies. The maximum efficiency of this system is about 1.8% and is achievable at the pressures between about 30-45 psi and flowrates between 1.05 and 1.3 L/s, as shown by the small dark strip 18 on the graph in the center of the data.

Comparing Table 4 with the graph of FIG. 14 it can be seen that, at any given pressure, there exists a flow rate at which the efficiency should be able to be about 1.4%-1.6%, or higher. The data in Table 4 reveal a decreasing efficiency with decreasing pressure, and from this, using the graph of FIG. 14, it may be understood that the inefficiency may be due to flowrate being less than optimal. For this specific pump, the flow rate is more optimal at higher pressure levels. Accordingly, for any given design to be deployed on a marine animal the turbine could be designed so that, at the pressure at which the first check valve will open, the inlet flow rate will be optimized for maximum efficiency. This may be done, for instance, by modifying the size of the inlet the turbine. A similar optimization may be done for the outlet side of such system, and in doing this the system may be able to achieve higher efficiencies. Nevertheless, even with these improvements, there are other improvements that could be made to the turbine design, described hereafter, which could increase efficiency more.

Figure 15:
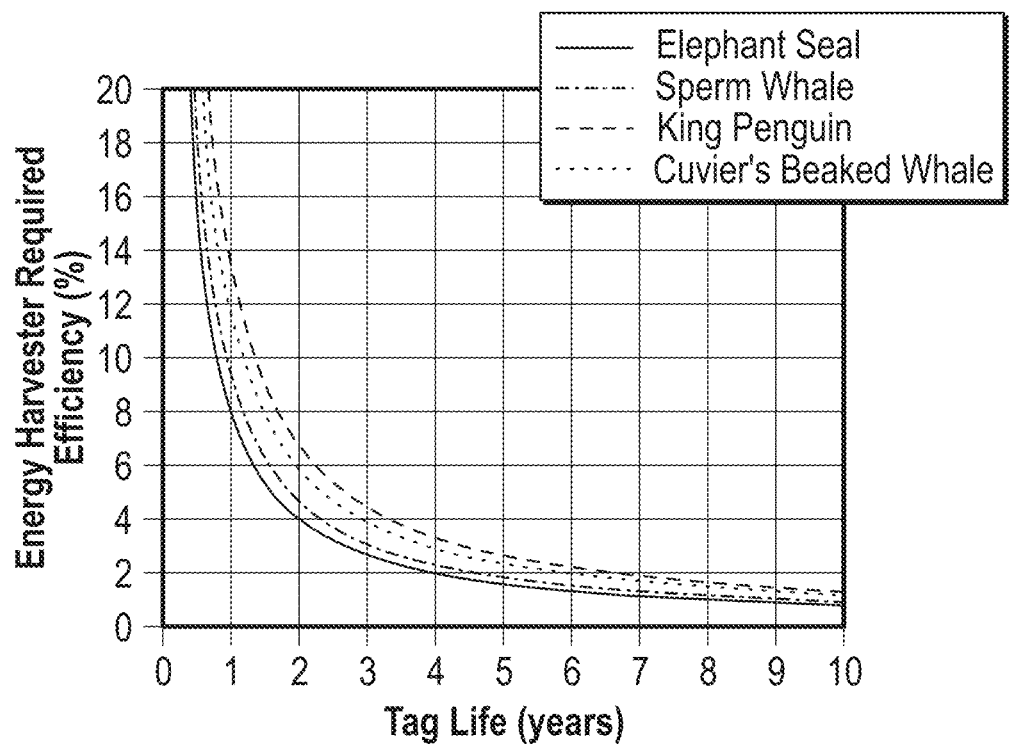
FIG. 15 is a graph depicting the required efficiencies for energy harvesters in order to outperform equivalently sized Li—SOCl$_2$ batteries.

Referring now to FIG. 15, a graph showing the required efficiencies for energy harvesters in order to outperform equivalently sized lithium-thionyl chloride (Li—$SOCl_2$) batteries is shown. This graph takes into account the energy density and volume of a Li—$SOCl_2$ battery, the volume and transduction efficiency of the energy harvester, and the frequency of the dives of a particular animal. Tag life is defined as the point at which an energy harvester system would provide the same energy per day as an equivalently sized battery. The tag life should not be interpreted as the expected lifetime of the harvester powered system, as the harvester could provide a much longer life than a battery system.

As can be seen in the graph, with increased tag life the required efficiencies are all less than 2% somewhere between 4 and 7 years of tag life. Several appear to require an efficiency of less than 1% to outperform the Li—$SOCl_2$ battery versions if they last for about 7 years or more.

Figure 16A:
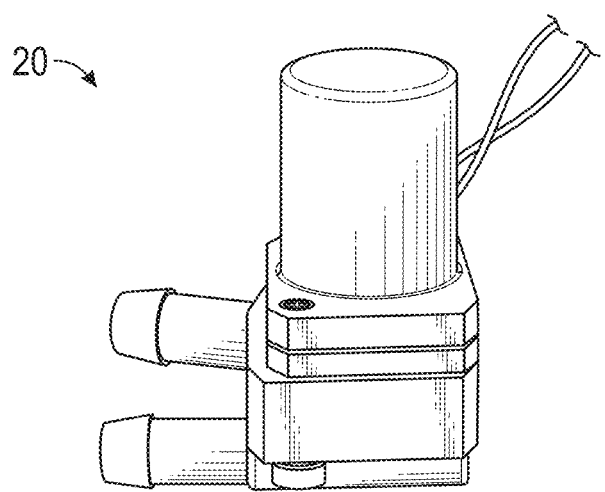
FIG. 16A is a side view of an implementation of the turbine/pump used in the experimental implementation of an energy harvesting system from FIG. 13.
Figure 16B:
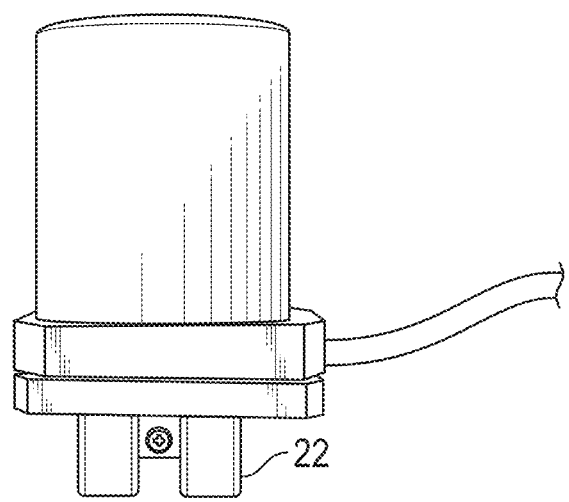
FIG. 16B is a side view of an implementation of the turbine/pump used in the experimental implementation of an energy harvesting system from FIG. 13 having the manifold removed.
Figure 16C:
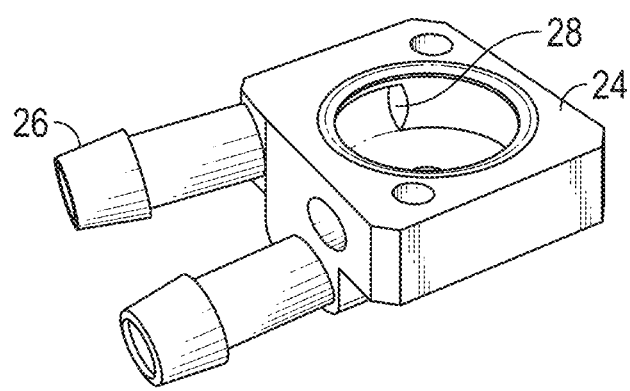
FIG. 16C is perspective view of the inner manifold from the implementation of the turbine/pump used in the experimental implementation of an energy harvesting system from FIG. 13.

Referring now to FIG. 16A-16C, the M200 pump 20 used as a turbine in the previously described implementation is illustrated. In FIG. 16A, the pump 20 is shown fully assembled. In FIG. 16B the lower manifold 24 is removed, exposing the impeller 22. In FIG. 16C, the lower manifold 24 is shown. The M200 pump was used in the experiment because it is an off-the-shelf pump able to be used as a turbine by operating in reverse. The images are given to show why the M200 pump is inherently inefficient when used as a turbine. The inlet 26 is actually the outlet when the device is run as a pump. A wall 28 faces the water as it enters the turbine from the inlet 26. The water hits this wall 28 and loses some of its momentum. Removing this wall 28 and angling the inlet 26 so that the incoming water faces the paddle wheel of the impeller more squarely will increase the efficiency.

Additionally, the inlet 26 pipe is too large. Decreasing the diameter of the inlet pipe will decrease the flow rate through the turbine while maintaining the same fluid jet velocity hitting the paddle wheel. This would effectively increase the time it takes for the pressure to equalize and, thus, the turbine will be powered for a longer period of time, increasing efficiency. These details are disclosed to show that the necessary efficiencies to make such energy harvesters viable are very likely feasible with a few turbine design changes.

Figure 17:
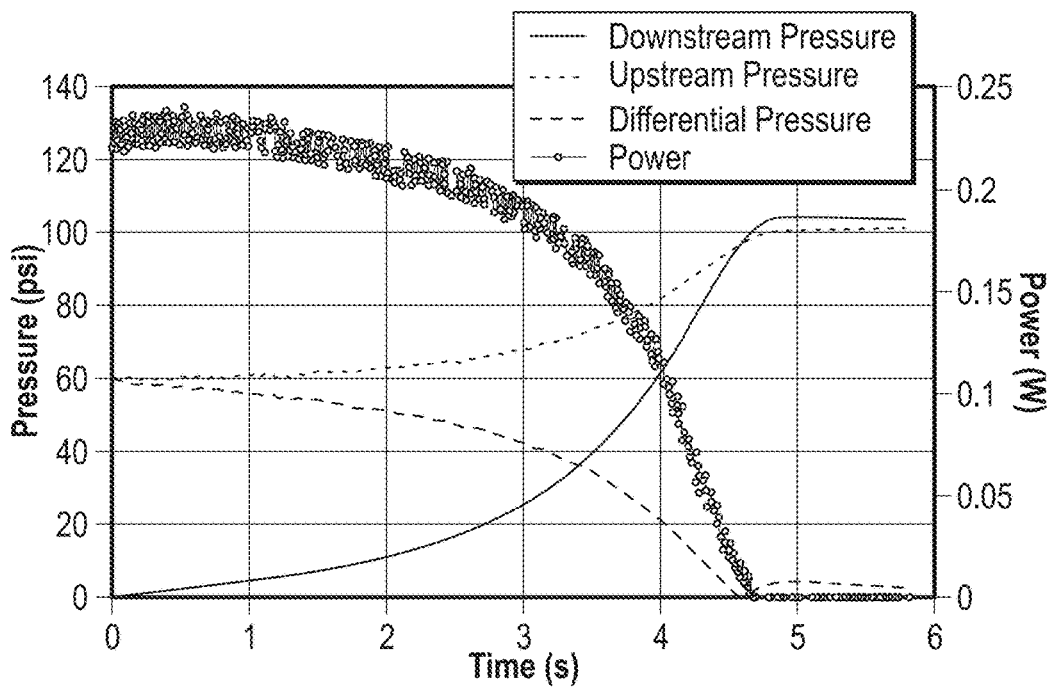
FIG. 17 is a graph depicting the change in pressure over time as an animal dives down and back up.

Referring now to FIG. 17, the graph highlights another area of inefficiency that may be improved upon. In the tests, a relatively long length of tubing was used to couple the pressurized water holding tank to the water turbine. The graph shows the upstream pressure (at the upstream pressure transducer of FIG. 13), the downstream pressure (at the downstream pressure transducer of FIG. 13), the differential pressure between these two and the power in Watts all plotted as a function of time. The data represents the 100 psi test of Table 4, but as can be seen the pressure at the inlet of the turbine starts out at 60 and does not reach 100 psi for almost 5 seconds. Thus, if there were less or shorter tubing coupling the pressurized water source to the turbine, the initial differential pressure would be greater.

Figure 18:
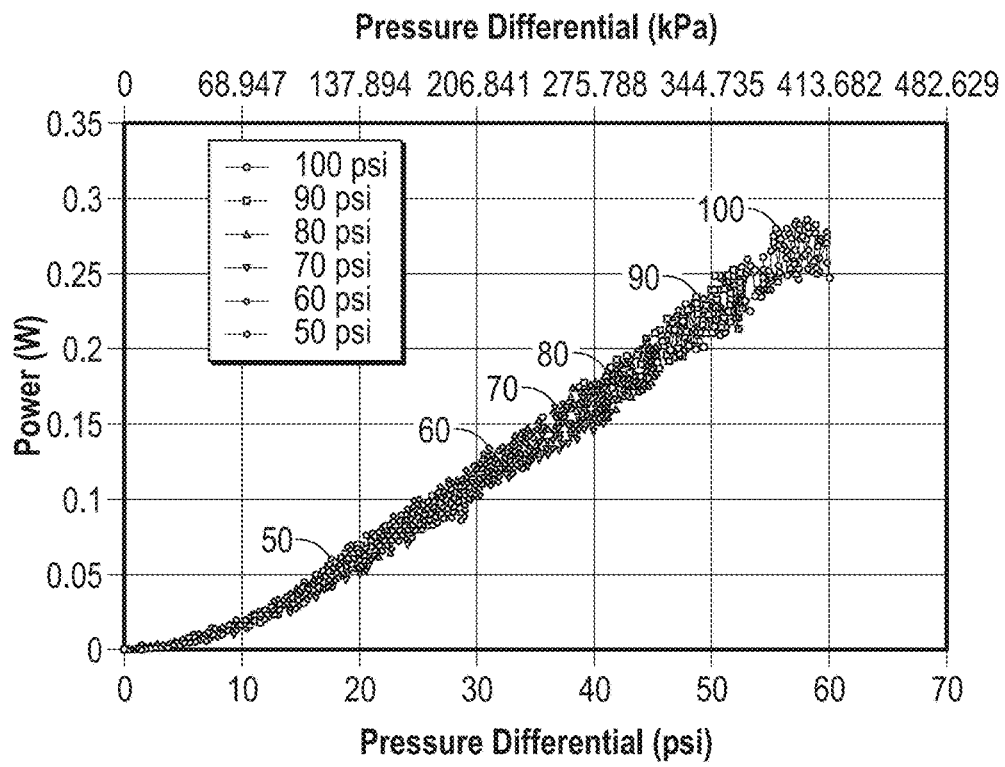
FIG. 18 is graph depicting the increase of power generation with increasing pressure.

Referring now to FIG. 18, a graph showing power in Watts versus pressure differential for the six tests in Table 4 is illustrated. The graph shows that the relationship between the pressure differential and the turbine's power output can be defined by a polynomial:

$$W_{turbine} = 5 \times 10^{-10}(\Delta p)^2 + 0.0005(\Delta p) - 13.591$$

where W is the output power (in mW), and $\Delta p$ is pressure differential (in Pa). This equation was created using a regression analysis and can be used to accurately characterize the turbine's power output based on the pressure differential across the turbine. However, it is only valid for pressures ranging up to 60 psi and below. The current M200 pumps begin to leak after being exposed to pressures greater than 110 psi and thus limit the ability to characterize the turbines beyond a pressure differential of 60 psi. Accordingly, a micro turbine designed for higher pressures may be designed and a polynomial expressing power versus differential pressure relationship may be modeled. From this model, the optimal conditions for pressure differential may be determined, to maximize total power, and the system designed accordingly for the valves to open and close at appropriate pressures, etc. Regarding the length of tubing, it may be understood that a system in use on a marine animal will have little to no tubing between the pressurized water source(s) and the turbine(s), and thus some of these inefficiencies will naturally not be included in an actual prototype to be deployed on a marine animal.

In places where the description above refers to particular implementations of an energy harvesting system and implementing components, sub-components, methods and sub-methods, it should be readily apparent that a number of modifications may be made without departing from the spirit thereof and that these implementations, implementing components, sub-components, methods and sub-methods may be applied to other energy harvesting systems.

What is claimed is:

1. An energy harvesting system comprising:
   an accumulator comprising an energy storage system separated from water by a membrane;
   one or more hydro turbines coupled with the accumulator;
   one or more check valves each coupled with one of the one or more hydro turbines;
   a power conditioner electrically coupled with each of the one or more hydro turbines;
   a system battery coupled to the power conditioner; and
   an electronic load coupled to the system battery through the power conditioner;
   wherein the one or more check valves are configured to be in contact with water;
   wherein the energy harvesting system is sized to couple with a monitor configured to couple with an animal.

2. The energy harvesting system of claim 1, wherein the energy storage system comprises an air bladder separated from the water by a membrane.

3. The energy harvesting system of claim 1, wherein the energy storage system comprises a spring coupled to the membrane wherein the membrane is configured to bias the spring in response to pressure force.

4. The energy harvesting system of claim 1, further comprising a secondary fluid reservoir coupled to an inlet and an outlet of the system, the secondary fluid reservoir comprising a working fluid separated from the water by a second membrane, wherein compression of the working fluid occurs in response to pressure force, storing energy in the energy storage system.

5. The energy harvesting system of claim 4, wherein the working fluid is one of fresh water and oil.

6. The energy harvesting system of claim 1, further comprising a second hydro turbine coupled with a second check valve.

7. The energy harvesting system of claim 1, wherein the electronic load comprises monitoring and communication equipment.

8. The energy harvesting system of claim 1, wherein the monitor is one of a bio-logger and a telemetry tag.

9. The energy harvesting system of claim 1, wherein the monitor is one of coupled to an inside and an outside of a system housing.

10. An energy harvesting system comprising:
    a first hydro turbine and a second hydro turbine, each turbine comprising an inlet and an outlet;
    a pressure accumulator comprising an energy storage system and a fluid section separated by a membrane, the pressure accumulator coupled with the outlet of the first hydro turbine and the inlet of the second hydro turbine;
    a first high-hysteresis check valve, coupled to the inlet of the first hydro turbine;
    a second high-hysteresis check valve, coupled to the outlet of the second hydro turbine;
    a power conditioner electrically coupled to the first and to the second hydro turbine;
    a system battery electrically coupled with the power conditioner; and
    an electronic load electrically coupled with the system battery through the power conditioner;
    wherein the first hydro turbine and the second hydro turbine are configured to generate electricity and charge the system battery when water flows into the first hysteresis check valve through the first hydro turbine and when water flows through the second hysteresis check valve from the pressure accumulator and through the hydro turbine;

wherein the energy harvesting system is sized to couple with a monitor configured to couple directly with an animal.

11. The energy harvesting system of claim 10, wherein the energy harvesting system comprises one or more springs and the membrane is configured to bias the one or more springs in response to pressure force.

12. The energy harvesting system of claim 10, wherein the energy harvesting system comprises an air bladder.

13. The energy harvesting system of claim 10, further comprising a secondary fluid reservoir coupled to an inlet and an outlet of the system, the secondary fluid reservoir comprising a working fluid separated from the water by a second membrane, wherein compression of the working fluid occurs in response to pressure force, storing energy in the energy storage system.

14. The energy harvesting system of claim 13, wherein the working fluid is one of water and oil.

15. The energy harvesting system of claim 10, wherein the electronic load comprises monitoring and communication equipment.

16. The energy harvesting system of claim 10, wherein the monitor is one of a bio-logger and a telemetry tag.

17. The energy harvesting system of claim 10, wherein the monitor is one of coupled to an inside and an outside of a system housing.

18. A method for powering an animal monitor, the method comprising:

receiving water at a first high hysteresis check valve wherein the water is moved by pressure force;
receiving the water at an inlet of a first hydro turbine coupled with the first high hysteresis check valve;
generating electricity for storage by a system battery using the first hydro turbine and the water;
receiving the water into a pressure accumulator and increasing a pressure of the pressure accumulator, the pressure accumulator coupled with the first hydro turbine;
receiving water at an inlet of a second hydro turbine from the pressure accumulator, the water moving under pressure force;
generating electricity for storage by the system battery using the second hydro turbine and the water;
receiving at a second high-hysteresis check valve the water from the second hydro turbine; and
releasing the water through the second high-hysteresis check valve;
wherein the system battery comprised within a system housing powers a monitor comprising circuitry and electronics, the monitor sized and configured to be coupled directly to an animal.

19. The method of claim 18, wherein the monitor is one of a telemetry tag and a bio-logger.

20. The method of claim 18, wherein the monitor is one of coupled to an inside and an outside of the system housing.

* * * * *

UNITED STATES PATENT AND TRADEMARK OFFICE
CERTIFICATE OF CORRECTION

PATENT NO. : 10,292,587 B2
APPLICATION NO. : 15/173540
DATED : May 21, 2019
INVENTOR(S) : Michael W. Shafer, Eric Morgan and Gregory Hahn It is certified that error appears in the above-identified patent and that said Letters Patent is hereby corrected as shown below:

In the Specification

Column 6, Line 18, delete "Joules (J) for the SPOTS", insert --Joules (J) for the SPOT5--

Signed and Sealed this
Ninth Day of July, 2019

Andrei Iancu
*Director of the United States Patent and Trademark Office*